United States Patent
Lorimer et al.

(10) Patent No.: US 7,467,048 B2
(45) Date of Patent: Dec. 16, 2008

(54) ELECTROCHEMICAL SENSOR

(75) Inventors: Kevin Lorimer, Abingdon (GB); John Griffiths, Derbyshire (GB); Mark Hyland, Oxford (GB)

(73) Assignee: Oxford Biosensors Limited, Oxon (GB)

( * ) Notice: Subject to any disclaimer, the term of this patent is extended or adjusted under 35 U.S.C. 154(b) by 0 days.

(21) Appl. No.: 11/660,400

(22) PCT Filed: Aug. 3, 2005

(86) PCT No.: PCT/GB2005/003050

§ 371 (c)(1),
(2), (4) Date: Feb. 15, 2007

(87) PCT Pub. No.: WO2006/018600

PCT Pub. Date: Feb. 23, 2006

(65) Prior Publication Data

US 2007/0276611 A1 Nov. 29, 2007

(30) Foreign Application Priority Data

Aug. 17, 2004 (GB) ................................. 0418346.3

(51) Int. Cl.
*G06F 19/00* (2006.01)
*G06F 15/00* (2006.01)

(52) U.S. Cl. .................. 702/32; 702/104; 702/189; 702/190

(58) Field of Classification Search .......... 702/33–38, 702/32, 104–107, 184–187, 189, 190, 116–126; 700/73, 74; 324/631, 457.4, 664, 667, 640, 324/675, 690
See application file for complete search history.

(56) References Cited

U.S. PATENT DOCUMENTS 3,766,411 A 10/1973 Arnold
4,072,594 A 2/1978 Outsuka et al.

OTHER PUBLICATIONS

Kuhlman et al. "Detecting heavy metals in solution using electronic-tongue 3 REDOX water quality sensors" Aerospace Conference, 2004. Proceedings. 2004 IEEE Big Sky, MT, USA Mar. 6-13, 2004, Piscataway, NF, USA, IEEE, US, Mar. 6, 2004, pp. 363-378 vol. 1, XP010747930.*
International Search Report corresponding to PCT/GB2005/003050, under date of mailing of Mar. 16, 2006.
Kuhlman, Gregory M, et al., Detecting Heavy Metals in Solution Using Electronic-Tongue 3 REDOX Water Quarlity Sensors, 2004 IEEE Aerospace Conference Proceedings, 2004, pp. 363-378, vol. 1, Piscataway, New Jersey, USA.
Whitaker, Stephen, et al., An Approach to . . . Numerical Differentiation of Experimental Data, Industrial and Engineering Chemistry, Feb. 1960, pp. 185-187, vol. 52, No. 2.
Better by Design: The Humanizing Technology Project, Medical Device Technology, Nov. 2003, Oxford Biosensors Ltd., United Kingdom.

* cited by examiner

*Primary Examiner*—Eliseo Ramos Feliciano
*Assistant Examiner*—Phuong Huynh
(74) *Attorney, Agent, or Firm*—Quarles & Brady; George E. Haas

(57) ABSTRACT

In an electrochemical sensor, a peak is detected by grouping data points in windows and detecting two or three windows between which the slope of the data changes sign. The peak can be more precisely detected by detecting the highest data point in the two or three windows.

13 Claims, 2 Drawing Sheets

ELECTROCHEMICAL SENSOR

The present invention relates to electrochemical sensors and electrochemical sensing methods.

In an electrochemical biosensor, a working electrode is used with a counter electrode and a reference electrode, though the latter two may be combined as a pseudo-reference electrode. In the text below, the term reference electrode should be construed as including pseudo-reference electrodes unless the context otherwise requires. To make a measurement, a potential difference is applied between the working and reference electrode and the resulting current is measured over a range of voltages. The analyte concentration and analyte species present in a fluid can be derived from current measurements at specific potential differences. Complementary information can be derived from the measured voltammetric peak position (and/or mid point position) and voltammetric peak separation. An electrode that can be used in such biosensors is described in WO 03/056319 (which document is hereby incorporated in its entirety by reference).

A particular problem with deriving information from the locations of voltammetric peaks is the determination of the location of the peaks themselves in the data derived from measurements on the sample. Often what is sought is a small peak on a larger slope so that a simple algorithm to find the highest value will return the wrong result.

Accordingly, the present invention provides an electrochemical sensing method comprising:

applying a time-varying potential between working and reference electrodes in electrical contact with a target solution;

sampling the current flowing between said working and reference electrodes at predetermined intervals;

deriving a plurality of data points, each data point comprising a potential value and a corresponding current value;

dividing said data points into a plurality of successive groups, each group comprising a plurality of successive data points;

determining the sign of the current/potential slope in each group; and finding a set of groups between which the sign of the current/potential slope changes.

This method provides a reliable, rapid and easily programmed method of locating a peak in voltammetric data derived from a target solution. Successive data points are divided into a series of groups, effectively windowing the data, and the slope of each group is determined. this can be obtained most simply as the slope of a line between the first and last data points of each group or by a linear fitting procedure. When the slope changes in two successive groups from positive to negative or vice versa, it can be deduced that the peak lies within the two groups. That may for some applications be a sufficient location of the peak but for a more accurate location, and/or a measurement of the height of the peak, the highest data point in the two groups can be located, or the data points of the two groups can be fitted to a theoretical model. A slope of zero can be considered to be either positive or negative as desired. Alternatively, the peak can be determined to be within the three groups over which the slope changes sign.

In a preferred embodiment of the invention, a plurality of successive measurements are averaged to derive each data point.

It is also preferred that the time-varying potential is a linear increase or decrease in potential and said data points are derived from measurements taken at equal predetermined intervals. For example, to detect a peak indicating the presence of cobalt in the target solution, a linear increase from about −0.6V to +1.6V at a rate of 50 mVs$^{-1}$ is suitable. Each data point may be averaged from several samples, to reduce noise, and grouped e.g. into groups of 5 points, which would result in 44 groups being created over the whole of the scan.

The present invention is further described below with reference to an exemplary embodiment and the accompanying drawings, in which.

Figure 1:
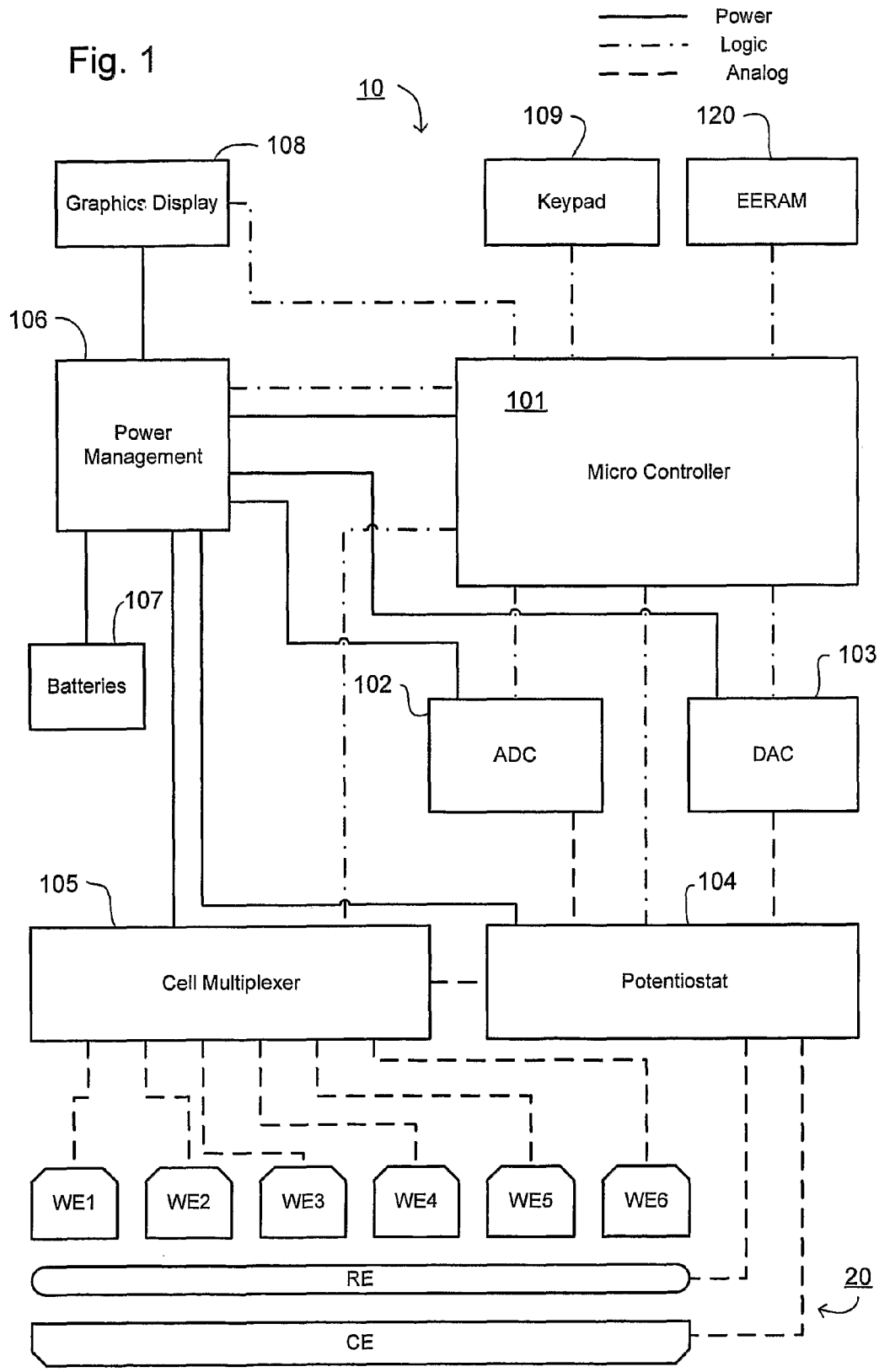
FIG. 1 is a schematic diagram of a portable electrochemical sensor device incorporating the invention.

As shown in FIG. 1, the sensor device comprises an electronics unit 10 to which is connected an electrode unit 20, which may be disposable. The electrode unit 20 has a plurality of working electrodes WE1-WE6 as well as reference and counter (auxiliary) electrodes RE, CE. Other embodiments may use more or fewer working electrodes. In some embodiments of the invention, the reference and counter electrodes may be combined to form a pseudo-reference electrode. An electrochemical cell is formed between the working and counter electrodes. To make measurements of a target solution that is in electrical connection with the electrodes, various voltages—static or time varying—are applied between ones of the working electrodes and the reference electrode and the resulting currents detected. For example, cobalt (Co) can be detected by applying a rising potential and detecting a current peak. A method of doing this is described further below.

Overall control of the electronics unit 10 of the sensor device is performed by a micro controller 101 which includes an internal memory to store system software. The micro controller may be a dedicated ASIC, an FPGA or a suitably programmed general purpose controller. The micro controller controls a potentiostat 104 via digital to analog converter 103 and receives measurement results from the potentiostat 102 via analog to digital converter 102. The potentiostat 104 applies the desired voltages to the working, reference and counter electrodes WE, RE, CE; a cell multiplexor 105 under the control of microprocessor 101 selects the appropriate one of the working electrodes. The electrodes are preferably micro-electrodes, e.g. having a width of less than about 50 μm, microband electrodes or a micro-electrode array.

A graphics display 108 enables display of operating menus to the user, options being input via keypad 109, and measurement results. An electrically erasable RAM 120 allows for storage of constants and measurement information. A bar code reader may also be provided for input of data, especially of patient information if the sensor is used in a medical or veterinarian application. Interfaces, e.g. conforming RS232, Bluetooth, Etherhet, USB, or WiFi (IEEE 802.11a, b, g, etc.) standards, may be provided for connection to printers, networks and other devices, e.g. patients records systems. The separately illustrated circuits may be combined onto one or more ASICs or FPGAs.

Power is supplied from batteries 107 under the control of a power management unit 106 that optimises battery life and controls recharging of the batteries.

Figure 2:
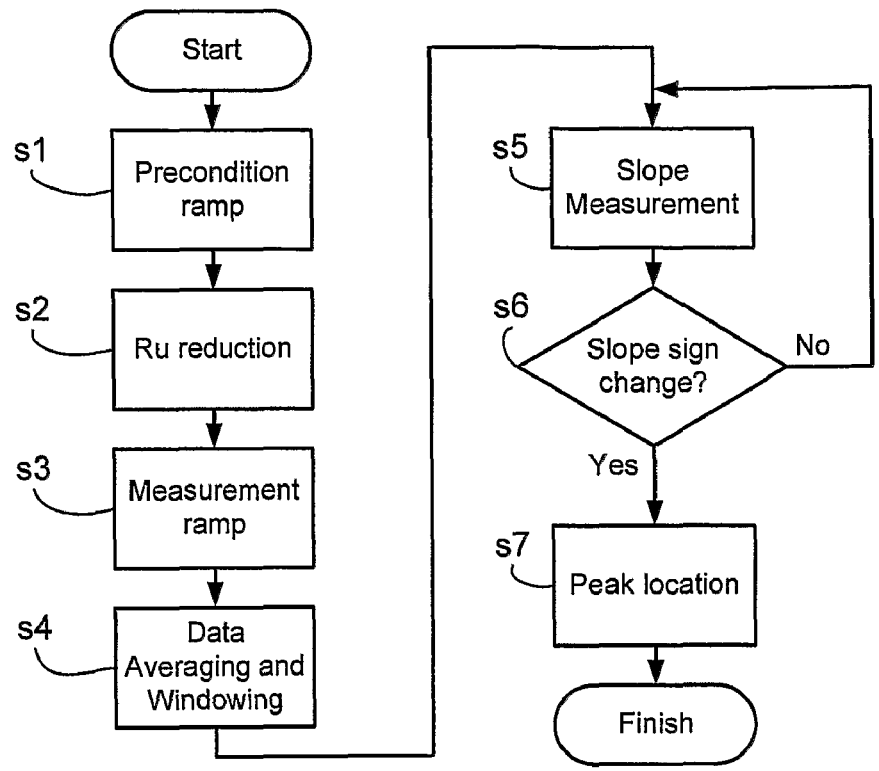
FIG. 2 is a flow diagram of a method according to an embodiment of the invention.

A flowchart of a process for detection and measurement of a cobalt peak is shown in FIG. 2. First of all, a preconditioning ramp potential from −0.5 to 1.6V is applied to the electrochemical cell in step s1. This can be performed at a relatively fast sweep rate, e.g. of 200-5000 mVs$^{-1}$ and may be omitted in some circumstances. Step s2 is a sweep from 0V to −0.5V to reduce any ruthenium present in the sample and may be omitted in some circumstances before the measurement ramp, step s3, during which the potential across the cell is raised from −0.5V to 1.6V at a rate of about 10-200 mVs$^{-1}$. Current measurements are taken at a rate of about 1-2 kHz, i.e. every 0.5-1 ms, so that there is a current measurement about every 50 μV. In step s4, successive measurements, e.g. 15 measurements or 15 ms worth of measurements, are averaged into data points to reduce noise. In effect, the current is sampled at predetermined intervals, e.g. every 10 mV. Successive data points are grouped, e.g. in groups of five and the slope of each group, or window, is determined in step s5, by determining the slope between the first and last data points of each group. If desired, the slope can instead be determined by an averaging or linear fitting process. At minimum, it is only necessary to determine whether the slope is positive or negative. A zero slope can also be identified or may be deemed to be either positive or negative. These operations can be performed only for the range in which the peak is expected, e.g. 1.1 to 1.6V for cobalt. In step s6, it is determined whether the slope of two adjacent groups (or three if one is zero) has changed from positive to negative. The converse test i.e. from negative to positive, may be used if a negative-going sweep is used instead.

A suitable program to effect the above process can be provided in the memory of the micro-controller or another memory in the device and executed by the device to give a detection and/or measurement of a peak of interest. Alternatively, the above described device may be used to collect measurement samples with the subsequent processing being carried out wholly or partially by an external computer system.

Detection of the two or three data point groups within which the slope changes may be sufficient localisation of the peak in some applications but if more accurate localisation is required, or a measurement of the current value at the peak is desired, the peak can be detected more precisely by determining which data point in the two or three groups is highest.

Figure 3:
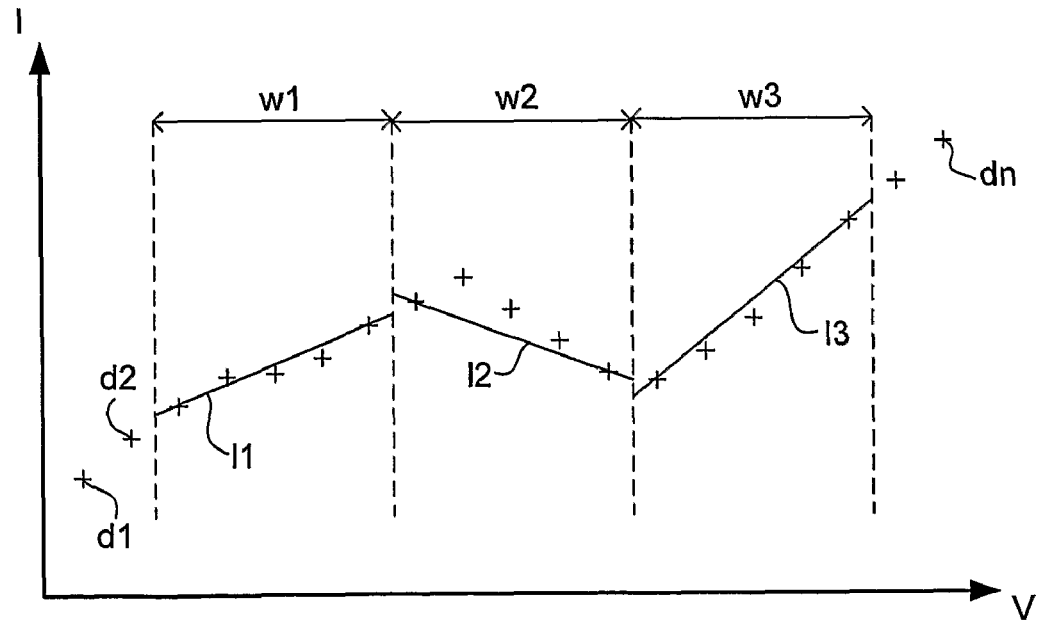
FIG. 3 is a graph of current vs. potential for a simplified example data set.

By way of illustration a simplified data set is plotted in FIG. 3. Data points d1 to dn are taken and divided into windows w1 to w3 covering the potential range set by the user. The slopes of the data points in each window is shown by lines 11, 12, 13, each joining the first and last data points in the group. It can be seen that the slope of 11 is positive and that of 12 is negative so the peak (point of inflection) is determined to lie in window w1 or w2. The ten data points can then be quickly examined to find the highest.

Whilst the invention has been described above in relation to a specific embodiment, the present invention may be embodied in other forms. It will be appreciated that details such as the rate of potential change during a sweep, the sampling rate, the averaging of samples into data points, and the number of data points in each window can be varied according to the species to be detected and experimental conditions. In some cases appropriate values may be found by trial and error using test or reference samples. Polarities in this document are defined using IUPAC conventions but the results can readily be converted to other conventions. The scope of the intention is therefore determined by the appended claims rather than the foregoing description.

The invention claimed is:

1. An electrochemical sensing method comprising:
applying a time-varying potential between working and reference electrodes in electrical contact with a target solution;
sampling the current flowing between said working and reference electrodes at predetermined intervals whilst said working and reference electrodes are in contact with said target solution to obtain a plurality of current samples;
deriving from said current samples a plurality of data points, each data point comprising a potential value and a corresponding current value;
dividing said data points into a plurality of successive groups, each group comprising a plurality of successive data points;
determining a sign of a current/potential slope in each group; and
detecting a peak in the plurality of data points by finding a set of groups between which the sign of the current/potential slope changes.

2. A method according to claim 1 wherein the slope of each of said groups is determined as the slope of a line between the first and last data points of each of said groups.

3. A method according to claim 1 wherein the slope of each of said groups is determined by a linear fitting procedure.

4. A method according to claim 1 comprising the further step of determining which of the data points in the set of groups is the highest.

5. A method according to claim 1 wherein a group having a slope of zero is considered to be of a predetermined sign.

6. A method according to claim 1 wherein said set of groups comprises two adjacent groups.

7. A method according to claim 1 wherein said set of groups comprises three adjacent groups, the middle one of which has a slope of zero.

8. A method according to claim 1 wherein a plurality of successive measurements are averaged to derive each data point.

9. A method according to claim 1 wherein said time-varying potential is a linear increase or decrease in potential.

10. A method according to claim 1 wherein said data points are derived from measurements taken at equal predetermined intervals.

11. A method according to claim 1 wherein said electrodes are micro-electrodes, microband electrodes or a micro-electrode array.

12. A computer program product for detecting a peak in voltammetric data derived from an electrochemical sensor, the program comprising instructions recorded on a computer-readable medium that, when executed on a computer system, instructs the computer system to effect steps of:
deriving a plurality of data points from samples of the current flowing from an electrochemical cell containing a target solution as a time-varying potential is applied to it, each data point comprising a potential value and a corresponding current value;
dividing said data points into a plurality of successive groups, each group comprising a plurality of successive data points;
determining the sign of the current/potential slope in each group; and
detecting a peak in the data points by finding a set of groups between which the sign of the current/potential slope changes.

13. An electrochemical sensor device comprising:
a potentiostat for applying a potential between working and reference electrodes in electrical contact with a target solution and sampling the current flowing between the electrodes;

a controller for controlling the potentiostat so that it applies a time varying potential and samples the current flowing between said working and reference electrodes at predetermined intervals whilst said working and reference electrodes are in contact with said target solution to obtain a plurality of current samples;

a data point generator arranged to derive from the current samples a plurality of data points, each data point comprising a potential value and a corresponding current value;

a group generator arranged to divide said data points into a plurality of successive groups, each group comprising a plurality of successive data points;

a slope calculator arranged to determine the sign of the current/potential slope in each group; and a point of inflection locator arranged to find a set of groups between which the sign of the current/potential slope changes.

* * * * *